United States Patent [19]

Mason

[11] Patent Number: 5,032,118
[45] Date of Patent: Jul. 16, 1991

[54] URINARY APPLIANCE

[76] Inventor: Lark E. Mason, 484 W. 43rd St., New York, N.Y. 10036

[21] Appl. No.: 611,887

[22] Filed: Nov. 13, 1990

[51] Int. Cl.⁵ .............................................. A61F 5/44
[52] U.S. Cl. ..................................... 604/349; 604/353
[58] Field of Search ............... 604/353, 350, 349, 322, 604/326, 323

[56] References Cited

U.S. PATENT DOCUMENTS

| | | |
|---|---|---|
| 525,925 | 9/1894 | Sahlstrom . |
| 2,494,477 | 1/1950 | Kurtz .................................. 128/295 |
| 2,937,645 | 5/1960 | Sachs .................................. 128/295 |
| 3,547,123 | 12/1970 | Sachs .................................. 128/295 |
| 3,721,243 | 3/1973 | Hesterman et al. ................ 604/353 |
| 4,511,358 | 4/1985 | Johnson, Jr. et al. .............. 604/353 |
| 4,553,968 | 11/1985 | Komis ................................ 604/349 |
| 4,713,066 | 12/1987 | Kohis ................................. 604/353 |
| 4,820,291 | 4/1989 | Terauchi ............................ 604/349 |

FOREIGN PATENT DOCUMENTS

A61F544 4/1980 PCT Int'l Appl. .
2016929 3/1979 United Kingdom .

Primary Examiner—Alan Cannon
Assistant Examiner—Debra S. Brittingham
Attorney, Agent, or Firm—Charles E. Temko

[57] ABSTRACT

An improved urinary device for use by male incontinent persons of the type in which a collector bag is supported upon the leg of the user. In lieu of the conventional leg-engaging straps, the collector bag is supported in a pocket on the outer surface of the leg member of an undergarment. The undergarment is made of highly resilient material including a lycra spandex component. The pocket is formed of relatively non-stretchable woven material and includes a rear wall extending from the waistband of the undergarment to a point below the lower edge of the pant leg, and a front wall approximately half the length of the rear wall and congruent with the lower half of the rear wall. A laminar type collector bag is carried within the pocket which has a lower opening for drainage. The rear wall of the pocket is stitched at the entire upper edge and side edges thereof to the undergarment to distribute the weight of a filled bag over a substantial area of the undergarment. This construction thus eliminates the concentration of the weight on the exposed leg of the wearer caused by leg engaging straps at the upper and lower part of the bag, which straps are eliminated.

3 Claims, 1 Drawing Sheet

URINARY APPLIANCE

BACKGROUND OF THE INVENTION

This invention relates generally to the field of male urinary appliances used by incontinent persons, and more particularly to an improved device for mounting a known-urine collecting bag upon the front surface of the thigh in an inconspicuous manner such that it can be periodically drained without disconnection from the patient. Devices of this general type are known in the art, and the invention lies in specific constructional details which permit improved comfort on the part of the user, as well as increased convenience in use.

At the present state of the art, there is a marked preference for a disposable bag formed from heat-sealed synthetic resinous material, such as polyethylene and the like, which can be used during the course of the working day, emptied periodically, and disposed of after a relatively short period of time without the necessity of restoring the same to sanitary condition. Such bags are fitted with a check valve at the upper edge thereof, and a drain tube at the lower edge which may be opened without disengaging the bag from the user.

The principal disadvantage of this type of construction is that it requires mounting means on the leg of the wearer in the form of upper and lower straps which are not only uncomfortable, but tend to inhibit circulation when the device is worn over a period of time. While the prior art has dealt with this problem to some degree, older constructions require the use of a specialized container which is not readily commercially available, and which is somewhat difficult to use.

SUMMARY OF THE INVENTION

Briefly stated, the invention contemplates the provision of an improved device for utilizing the above-described presently available collection bag, without the necessity of employing either of the upper an lower leg engaging straps. To this end, the inventive structure comprises an elastic undergarment, the body of which is formed from tightly knitted nylon including a lycra spandex component. The garment includes an adjustable elastic waistband, and elastic terminal edges at the lower ends of the pant legs. An inelastic pocket element is formed of heavy duty woven material. The pocket includes a rear wall of rectangular elongated configuration having an upper edge which terminates at the waistband and a lower edge which extends below the lower edge of the pant leg upon which it is mounted. The longitudinal edges of the rear member are stitched to the outer surface of the pant leg along the entire length of the latter. A corresponding front wall is stitched in congruent relation to the lower half of the rear wall along the side and lower edges thereof leaving a free upper edge for the insertion of the collector bag. A small opening at the lower edge of the pocket accommodates a drain tube of the bag. As the bag fills, the weight of the contents is transferred to the rear wall of the pocket and to the resilient pant leg over substantially the entire length of the forward surface thereof, which, through a relatively small degree of stretch, supports the entire weight without substantial increase in constrictive force upon the leg of the user.

BRIEF DESCRIPTION OF THE DRAWING

In the drawing, to which reference will be made in the specification, similar reference characters have been employed to designate corresponding parts throughout the several views.

Figures 1, 2, 3:
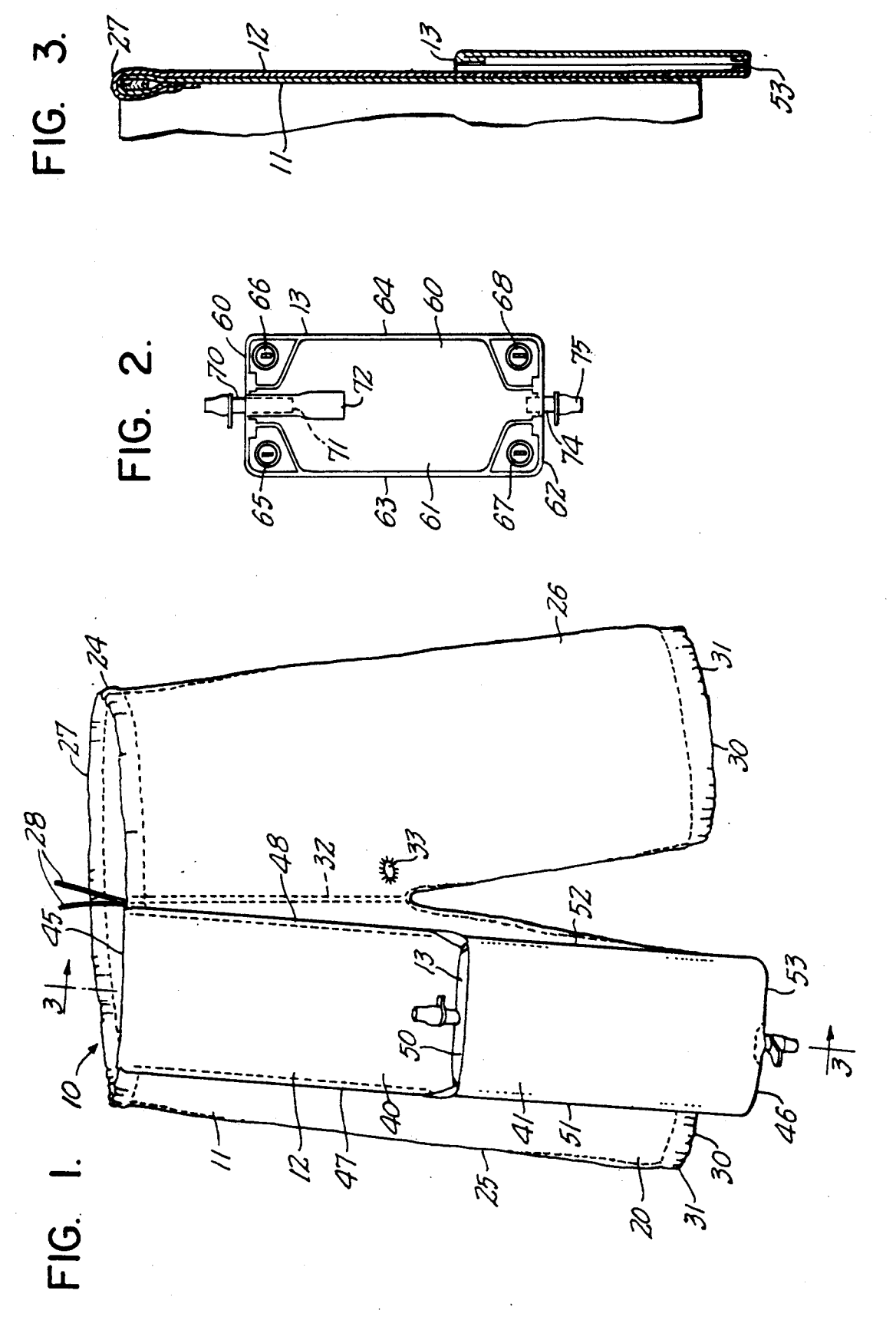

FIG. 1 is a front elevational view of an embodiment of the invention including a known collector leg bag.

FIG. 2 is a front elevational view of the collector bag used with the construction shown in FIG. 1.

FIG. 3 is a vertical sectional view, as seen from the plane 3—3 in FIG. 1.

DETAILED DESCRIPTION OF THE DISCLOSED EMBODIMENT

In accordance with the invention, the device, generally indicated by reference character 10, comprises broadly: a leg-engaging undergarment 11, an interconnected pocket element 12, and a collector bag 13.

The undergarment 11 is formed of knitted material, of a gauge substantially heavier than that employed for underwear, and similar to a type often used for sporting purposes. It will normally include about 15% of LYCRA spandex (E. I. Du Pont & Co.). It includes first and second forward panels 20 and 21, as well as corresponding third and fourth panels (not shown) which are interconnected to form an upper waist-enclosing portion 24, and first and second pant legs 25 and 26. The garment is bounded by an upper waist-engaging edge 27 which preferably includes a draw string 28. Each of the pant legs 25 and 26 terminates in a lower edge 30 which may include an elastic band 31. A centrally disposed vertical seam 32 adjoins a small opening 33 accommodating a collection tube (not shown).

The pocket element 12, by contrast, is formed of relatively inextensible material, preferably woven heavy duty cotton. It includes a rear wall member 40 and a front wall member 41.

The rear wall member 40 is of elongated rectangular configuration, and is bounded by an upper edge 45 which is stitched to the waistband 27 as well as a free lower edge 46 which extends below the edge 30 of the pant leg upon which it is mounted. Side edges 47 and 48 are stitched to the front panel 20 to the extent that they overlie the same.

The front wall member 41 is of configuration corresponding substantially to the lower half of the rear wall member, and is bounded by an upper free edge 50, as well as interconnected, e.g. stitched side edges 51 and 52 and lower edge 53. The upper edge 50 forms an opening leading to a recess which accommodates the collector bag 13.

The collector bag 13 is of well-known type, preferably formed of heat-sealed polyethylene. It includes a pair of side walls 60 interconnected at the upper edges 61, lower edges 62, and side edges 63 and 64. The corners include strap-engaging means 65, 66, 67 and 68, which are not employed.

The upper edge 61 incorporates an inlet tube 70, a lower end 71 of which is provided with a check valve 72 which prevents return of urine therethrough. The lower edge 62 incorporates a drain tube 74 provided with a removable cap 75 which permits draining at convenient intervals. This operation is facilitated by the fact that the pocket extends below the lower edge of the respective pant leg. Thus, although the garment exerts a general constrictive effect upon the torso of the wearer, it is distributed over the entire surface of the engaged body of the user, and not localized, as would be the case where leg straps are used. Once the bag becomes completely filled, a degree of stretch occurs in one pant leg, but because this load is also distributed over the entire length of the pant leg, the wearer is hardly aware of the fact that this has occurred. Thus, the device can be worn for long hours without any discomfort, and the convenience of using standard readily available collection bags which are readily replaceable, contributes to the utility of the device.

I wish it to be understood that I do not consider the invention to be limited to the precise details of structure shown and set forth in the specification, for obvious modifications will occur to those skilled in the art to which the invention pertains.

I claim:

1. An improved urinary appliance comprising: a leg-engaging undergarment, an interconnected pocket element, and a pocket engaging collector bag; said undergarment being formed substantially of knitted material having a component of spandex, and including an elastic waistband and first and second leg encircling portions defining forward and rearward surfaces and a pair of lower edges; said pocket element being formed of relatively inextensible material and including an inner wall of rectangular configuration bounded by an upper edge, a lower edge, and first and second side edges, said upper edge being stitched to said waistband, said side edges being stitched to said forward surface of one of said leg-encircling portions, said lower edge extending below said corresponding one of said pair of lower edges; said pocket element including an upper wall of configuration corresponding to substantially a lower half of said inner wall, and bounded by a free upper edge, first and second side edges, and a lower edge interconnected in congruent relation to said lower half of said inner wall to define an elongated recess therebetween; said collector bag being of generally rectangular planar configuration, and slideably engaged within said recess; whereby, upon the progressive filling of said bag, the increased weight thereof is supported by the slight stretching of the interconnected areas of said waistband and said one of said leg-encircling portions of said undergarment.

2. A urinary appliance in accordance with claim 1, further characterized in said pocket element being formed of woven material.

3. A urinary appliance in accordance with claim 1, further characterized in said collector bag having a tubular lower drain, said pocket element having a corresponding opening at said lower stitched edge, said tubular drain projecting through said opening.

* * * * *